(12) United States Patent
Bishop

(10) Patent No.: US 10,376,405 B2
(45) Date of Patent: Aug. 13, 2019

(54) BISHOP TRACTION SPLINT DEVICE (BTSD)

(71) Applicant: James Martin Bishop, Carleton, MI (US)

(72) Inventor: James Martin Bishop, Carleton, MI (US)

( * ) Notice: Subject to any disclaimer, the term of this patent is extended or adjusted under 35 U.S.C. 154(b) by 227 days.

(21) Appl. No.: 15/495,562

(22) Filed: Apr. 24, 2017

(65) Prior Publication Data

US 2017/0273817 A1    Sep. 28, 2017

(51) Int. Cl.
*A61F 5/058* (2006.01)
*A61F 5/048* (2006.01)
*A61F 5/04* (2006.01)

(52) U.S. Cl.
CPC ............ *A61F 5/0585* (2013.01); *A61F 5/048* (2013.01); *A61F 5/05841* (2013.01); *A61F 5/04* (2013.01)

(58) Field of Classification Search
CPC ........ A61F 5/0585; A61F 5/048; A61F 5/042; A61F 5/04
See application file for complete search history.

(56) References Cited

U.S. PATENT DOCUMENTS

| | | | | |
|---|---|---|---|---|
| 1,070,467 A | * | 8/1913 | Heggen | A61F 5/028 602/19 |
| 3,663,972 A | * | 5/1972 | Denton | A61G 1/00 5/625 |
| 4,181,125 A | * | 1/1980 | Carlson | A61H 1/0218 602/33 |
| 4,282,868 A | * | 8/1981 | Riggs | A61H 1/0218 482/131 |
| 4,911,152 A | * | 3/1990 | Barnes | A61F 5/0585 602/23 |
| 5,025,802 A | * | 6/1991 | Laico | A61G 13/12 128/875 |
| 5,342,288 A | * | 8/1994 | Lee | A61F 5/048 602/5 |
| 5,891,066 A | * | 4/1999 | Borschneck | A61F 5/04 602/5 |
| 5,895,367 A | * | 4/1999 | Mautoni | A61F 5/3776 602/32 |
| 9,180,037 B1 | * | 11/2015 | Smith | A61F 5/01 |

* cited by examiner

*Primary Examiner* — Kristen Matter
(74) *Attorney, Agent, or Firm* — Carrier Blackman & Associates, P.C.; Joseph P. Carrier; William D. Blackman

(57) ABSTRACT

The Bishop Traction Splint Device (BTSD) is a traction device for applying traction to a fractured leg. The device includes a frame for securing both legs in order to allow the uninjured leg to help splint the injured leg. A ratchet assembly located on a distal end of the frame is attached to an ankle brace on the injured leg to apply the traction force. Shoulder straps, an abdominal strap, and leg straps are used to secure the patient. A tripod assembly can also be sued to elevate both legs of the patient, placing the patient in a shock position to aid with any drop in blood pressure.

6 Claims, 6 Drawing Sheets

BISHOP TRACTION SPLINT DEVICE (BTSD)

BACKGROUND OF THE INVENTION

Field of the Invention

This invention, referred to as the Bishop Traction Splint Device (BTSD), is a modification of expired U.S. Pat. No. 5,342,288A, and relates to devices for applying traction to injured legs. Outside of the specific and unique changes to this device described herein the above referenced patent can be referred to for additional information as needed.

FIGS. 1 and 2 show two of the original drawings of the device disclosed in U.S. Pat. No. 5,342,288A without reference characters. The prior art device was created to stabilize a unilateral (i.e., . . . one leg) closed mid shaft femur fracture by the use of held in place mechanical traction. The device has parallel telescoping rails made from the frame itself. These rails allow the device to be adjusted and sized for various heights of patients using this device. These rails lock in the position the medical provider deems correct. To start the traction application process, if not ankle break is present, a medically trained individual must first apply an ankle brace having a loops attached to the bottom of it to the injured leg. The provider will then pull manual traction using the ankle of the injured leg in a directional manner meant to realign the broken femur to its normal position prior to the break. The goal is to stretch the shortened injured leg until it meets the length of the non-injured leg. The force needed to reach this position is then matched by the device's mechanical ability to recreate the same amount of force the provider used to hold the leg in proper place. The prior art device then uses a strap that wraps around the whole upper portion of the injured leg (e.g . . . ischium/groin/thigh area) as an anchor point the device will use to pull traction against. After this groin strap is secured, the device has a ratchet strap that can now be attached to the ankle brace loop mentioned above. Traction is then applied using a hand turned dial located on the device end to pull the leg taught until it matches the manual force applied by the provider. Once the desired outcome is reached. the device is then secured in place to inhibit any further movement until further medical care is required.

BRIEF DESCRIPTION OF THE DRAWINGS

Other objects and advantages will be apparent from the following description when taken in connection with the accompanying drawings in which.

DETAILED DESCRIPTION OF THE INVENTION

The BTSD applies traction to an injured leg. The key differences the device has over the prior art include:
1) Better overall stabilization to the injured leg;
2) A simpler and more practical application that allows the uninjured leg to be part of the stabilization process;
3) A less painful, more effective and overall safer means of traction being applied;
4) The ability of the ratchet assembly to slide and lock into grooved or notched positions found on the device frame;
5) The ratchet assembly including an adapter on each side of the assembly that will accept a handheld wretch device to allow better leverage during use; and
6) The option of the shock position for unstable patients.

The BTSD utilizes similar aspects, specs and materials as those found in the device of U.S. Pat. No. 5,342,288A as apparent to one of ordinary skill in the art from the instant disclosure.

Figure 1:
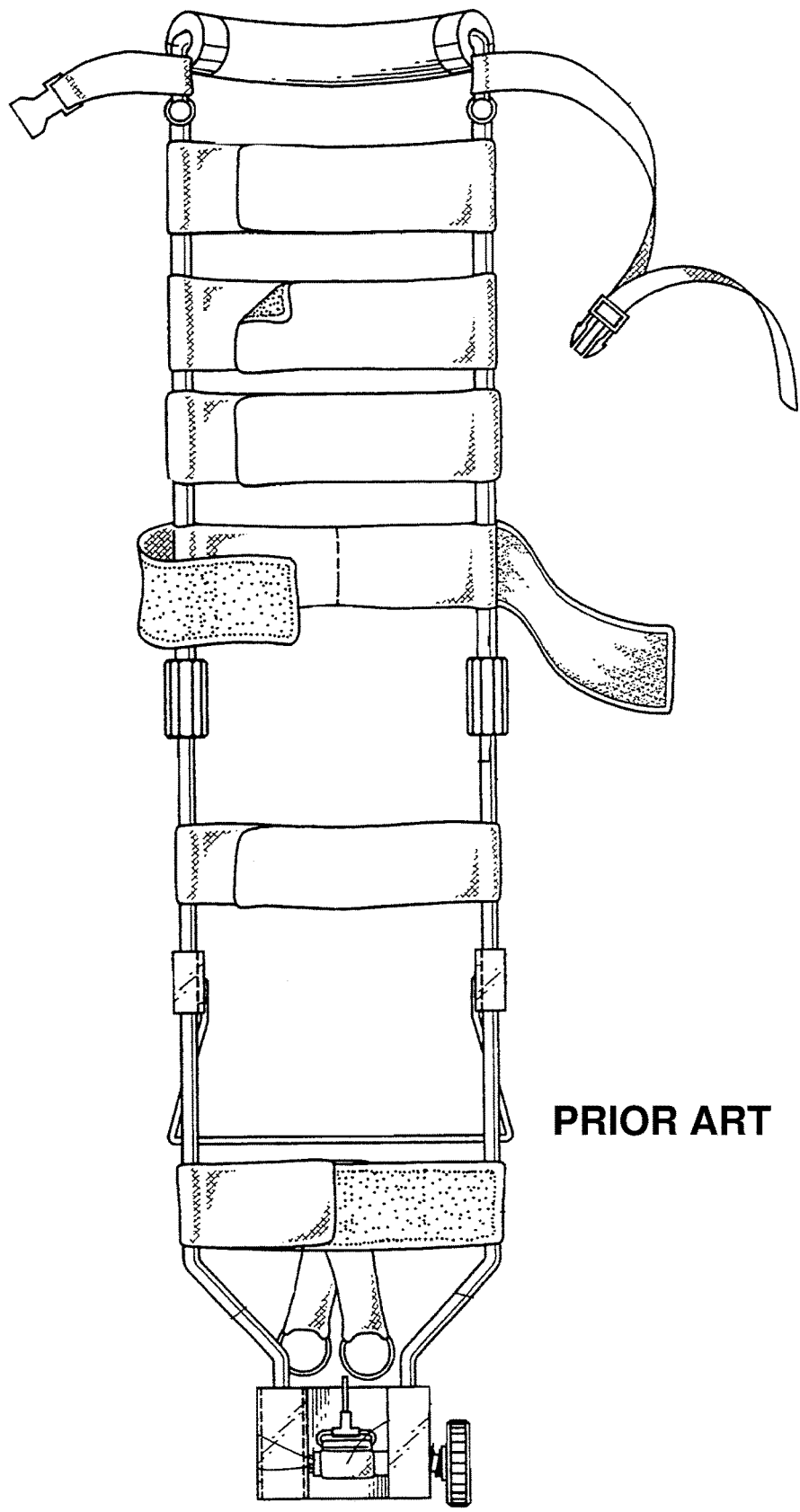
FIG. 1 is a general overview layout of the prior art device of U.S. Pat. No. 5,342,288A.
Figure 2:
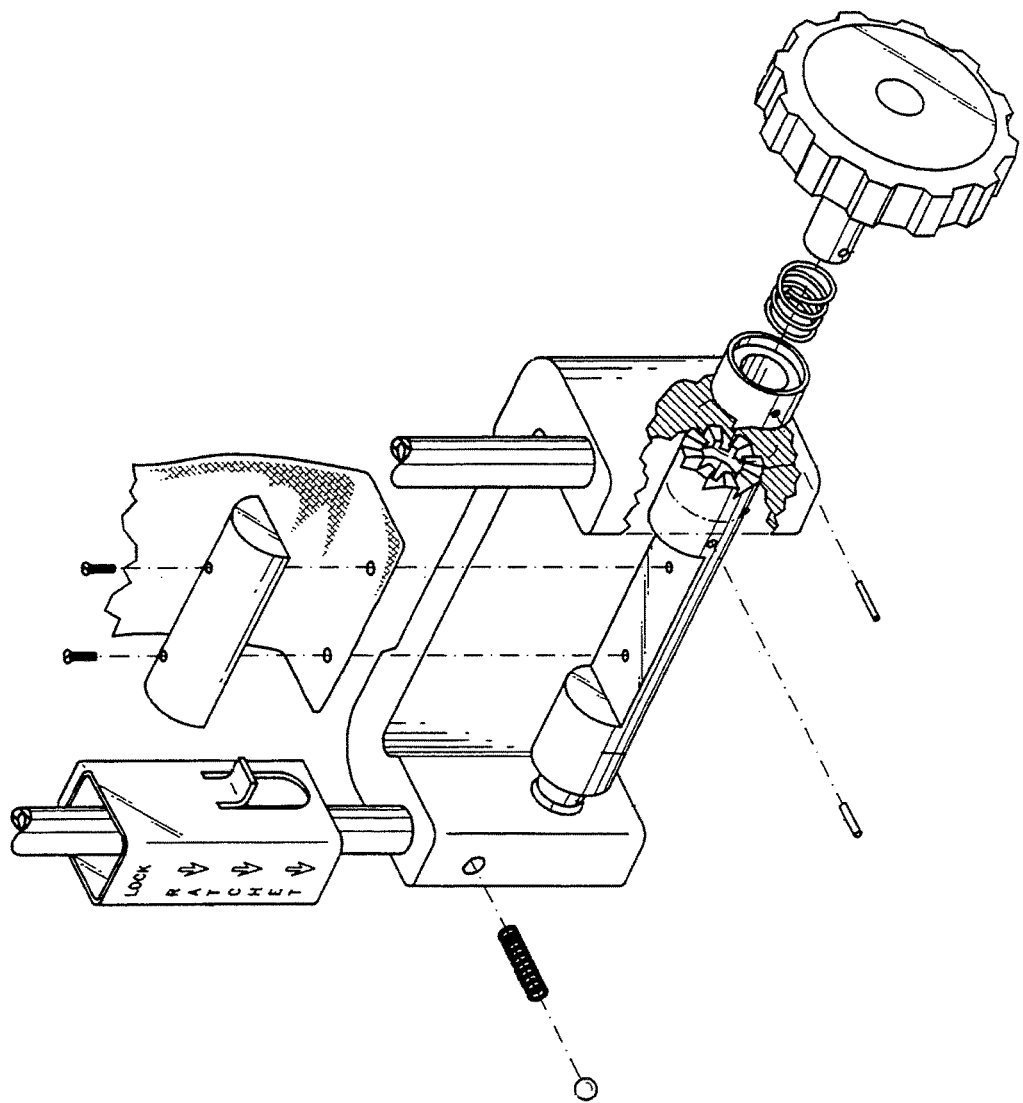
FIG. 2 is an exploded view of the prior art device ratchet assembly.
Figure 3:
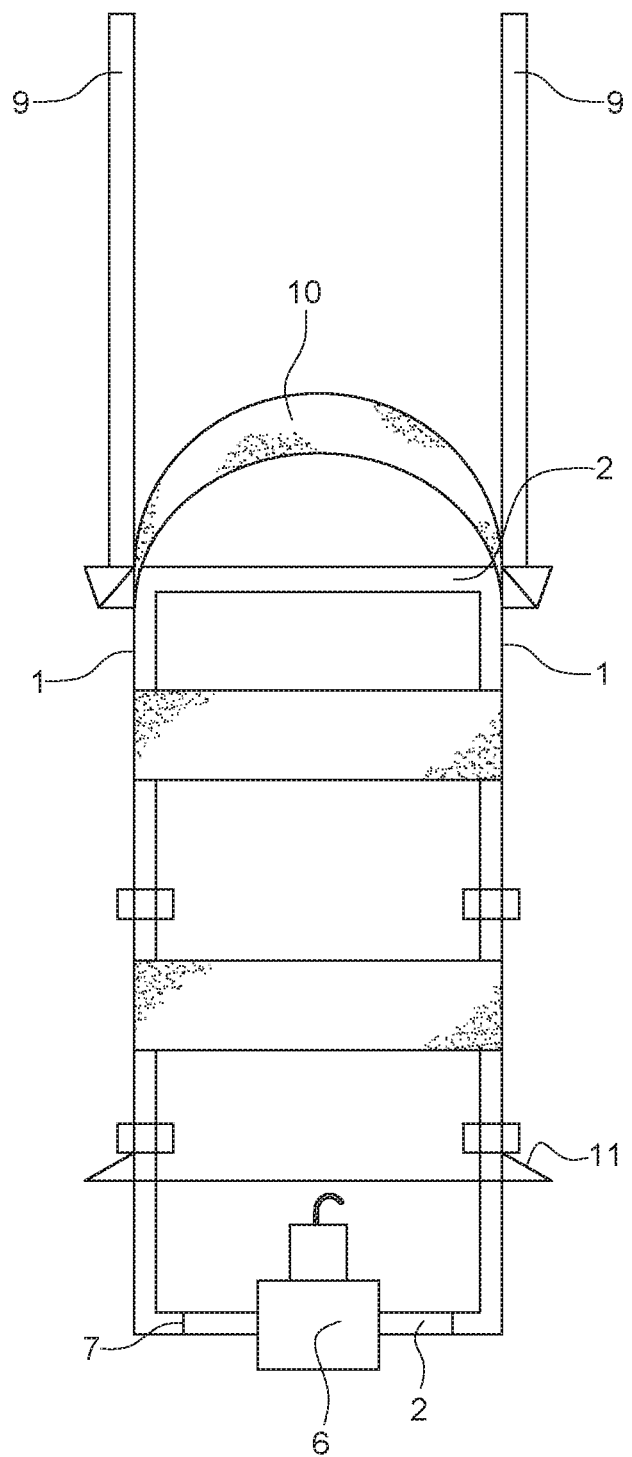
FIG. 3 is a back view of the BTSD.
Figure 4:
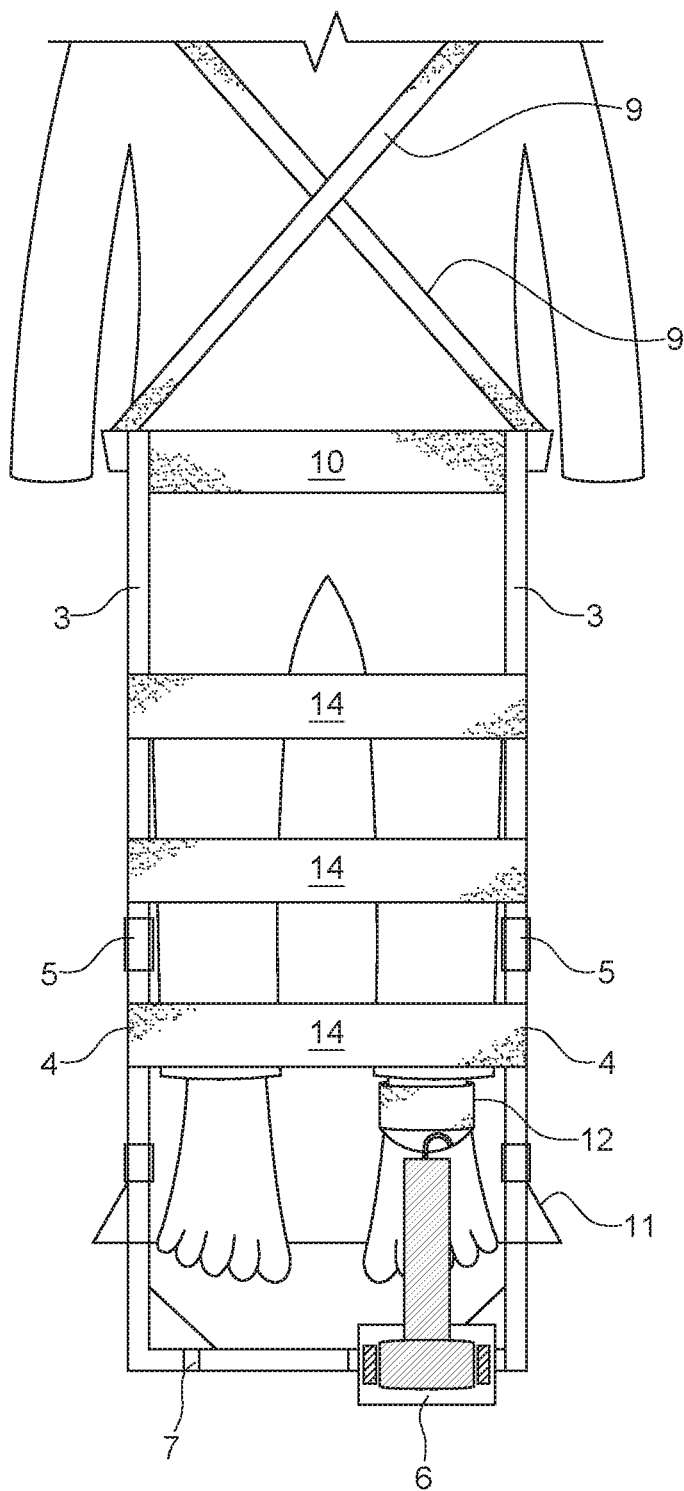
FIGS. 4 and 5 show the BTSD being used on a patient.
Figure 5:
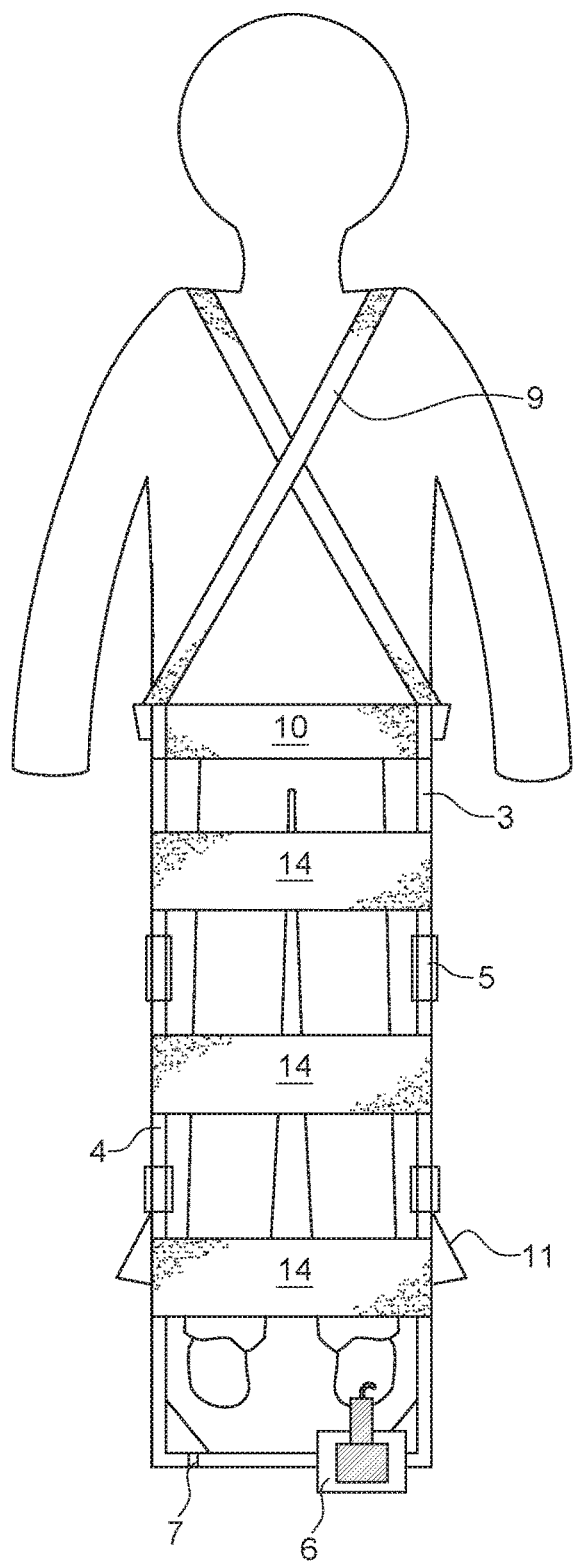
Figure 6:
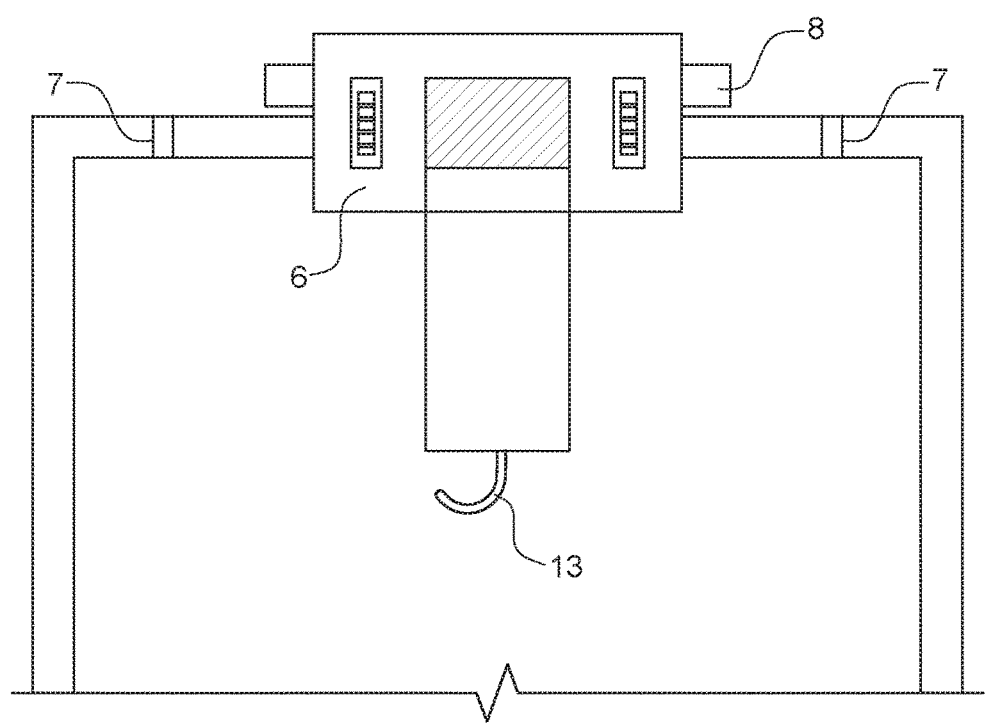
FIG. 6 shows the BTSD ratchet assembly with the ability to slide freely on the frame until locked into a chosen position.

The prior art device only utilizes the injured leg during application, while the BTSD is secured around both legs as shown in FIGS. 4 and 5. By securing both legs to each other after applying traction, the legs now become a natural splint for one another, which offers a secondary means of stabilization and immobilization after the desired traction is achieved. As seen in FIG. 3, the instant device has a squared off distal end. The device includes a rectangular frame having two parallel vertical members (1) and two parallel horizontal members (2) that are connected at a perpendicular angle to the vertical members to form the rectangular frame. Each of the vertical members includes a tube (3) that telescopically receives a rod (4) for adjusting the length of the vertical member to accommodate patients with different leg lengths. The rods are locked into a desired position by a releasable locking device (5), which is known in the art.

A ratchet assembly (6) is located on the distal horizontal member. The ratchet assembly is able to slide along the distal horizontal member such that the ratchet assembly can be positioned under either the left or right leg, depending on which leg is injured, and locked into place in grooves (7) provided on each side of the distal horizontal member. The ratchet assembly (6) includes a hand lever attachment site (8) on each of the left and right sides that is able to accept a handheld turning device (e.g., lever) for a more stable uninterrupted turn while applying traction and to allow the provider to achieve more leverage while traction force is being applied without chance of a premature release, which can be painful to the patient. The handheld turning device can come as a separately attachable tool or pre-attached to the ratchet assembly (6).

Dual shoulder straps (9) attach to the proximal end of the frame for using the shoulders and upper body of the patient as an anchor point as opposed to an injured leg. These straps can be applied in a crisscross or parallel arrangement. The prior art device anchors itself to the ischium/pubic/thigh area of the injured leg using a strap. This strap is meant to keep the device attached to the leg so that once traction is applied the device will stay in place allowing the leg to be pulled away from the hip for realignment. However, this ischium/pubic/thigh area strap has a tendency to slide down the leg, potentially injuring the patient and resulting in a loss of traction which can be painful to the patient because the entire process must be restarted. The BTSD traction device also includes a secondary abdominal strap (10) attached to the frame for additional securing means if needed.

The BTSD device also includes a tripod assembly (11) for elevating the splint. Because the device is secured over both legs, it allows both legs to be elevated together, placing the patient in a shock position to aid with any drop in blood pressure. The shock position is done with priority trauma patients and is achieved by elevating both legs while the patient remains flat on his or her back in order to shunt blood from the legs to the core of the body. The tripod assembly is made from bended steel and is designed to lock in place once it is set in either an elevated or non-elevated position. A rubber coating is applied to the portion of the tripod that makes contact with a supporting surface such as concrete, gravel, grass, snow, or bed linen. This action minimizes the possibility that the device will split on the surface and be painful to the patient.

In operation, an ankle brace/strap (12) is applied to an injured leg. The vertical members (1) are then adjusted to their desired length. The ratchet assembly (6) is locked into place on either the left or right side of the device to be located under the injured leg. A provider then carefully guides the device into position under the patient's legs Once in position, the shoulder straps (9) are secured to the patient and the ankle brace/strap (12) is attached to the ratchet assembly (6) by use of a loop on the ankle strap connecting to a hook (13) on the ratchet assembly. The handheld turning device is attached to a desired side of the ratchet assembly, if necessary, and the provider begins applying traction to the injured leg. The provider continues turning the turning device until the injured leg is pulled enough to realign the fracture. Once the desired amount of traction is achieved, the injured leg is further secured to the device with hook and loop leg straps (14) attached along the vertical members as seen in FIG. 4, using the opposite leg as a secondary means of splinting. Once all leg straps are secured, the abdominal strap (10) is fastened around the patient in order to help minimize movement of the patient during care and transportation. If needed, the tripod assembly (11) is set into the elevated position to place the patient in the shock position.

What is claimed is:

1. A traction splint device comprising:
   a rectangular frame comprising two vertical members and two horizontal members, the horizontal members being sized and configured to be placed under both legs of a patient, the vertical members each comprising a tube that telescopically receives a rod and a releasable locking device for locking the rod and tube in a desired position to accommodate a leg length of the patient;
   a ratchet assembly located on a distal one of the horizontal members for applying traction to a leg of the patient;
   an ankle brace configured to be secured to an ankle of the patient, the ankle brace being releaseably attached to the ratchet assembly to apply the traction;
   a tripod assembly for elevating the device and both legs of the patient thereby placing the patient in a shock position to aid with any drop in blood pressure;
   an abdominal strap attached to the frame and configured to be secured around an abdominal area of the patient; and
   leg straps configured to secure the legs of the patient in place once a desired amount of traction has been applied.

2. The traction splint device of claim 1, wherein the ratchet assembly further comprises a hand lever attachment site on each of a left side and a right side of the ratchet assembly, the hand lever attachment site configured to accept a handheld turning device or being pre-attached to the handheld turning device.

3. The traction splint device of claim 1, further comprising shoulder straps configured to anchor the device to an upper body of the patient for additional securing means.

4. The traction splint device of claim 1, further comprising a rubber coating applied to a portion of the tripod assembly configured to makes contact with a supporting surface.

5. The device of claim 1, wherein the ratchet assembly is slidable along the distal horizontal member such that it can be placed under either leg of the patient for applying traction.

6. The traction splint device of claim 1, wherein the leg straps jointly secure both legs of the patient to the rectangular frame such that one of the legs functions as a secondary splint for the other leg.

* * * * *